United States Patent
Mao et al.

(10) Patent No.: US 9,024,030 B2
(45) Date of Patent: May 5, 2015

(54) PROCESS FOR THE SYNTHESIS OF ETORICOXIB

(71) Applicants: Alfred E. Tiefenbacher (GmbH & Co. KG), Hamburg (DE); Shanghai Golden Pharmatech Co., Ltd., Shanghai (CN)

(72) Inventors: Zhenmin Mao, Shanghai (CN); Tian Lan, Shanghai (CN); Lanfang Liu, Shanghai (CN); Long Yan, Shanghai (CN); Stefan Becker, Hamburg (DE)

(73) Assignees: Alfred E. Tiefenbacher (GmbH & Co. KG), Hamburg (DE); Shanghai Golden Pharmatech Co. Ltd., Shanghai (CN)

( * ) Notice: Subject to any disclaimer, the term of this patent is extended or adjusted under 35 U.S.C. 154(b) by 0 days.

(21) Appl. No.: 14/371,540

(22) PCT Filed: Jan. 11, 2013

(86) PCT No.: PCT/EP2013/000071
§ 371 (c)(1),
(2) Date: Jul. 10, 2014

(87) PCT Pub. No.: WO2013/104546
PCT Pub. Date: Jul. 18, 2013

(65) Prior Publication Data
US 2015/0011771 A1 Jan. 8, 2015

Related U.S. Application Data

(60) Provisional application No. 61/600,819, filed on Feb. 20, 2012.

(30) Foreign Application Priority Data

Jan. 13, 2012 (CN) .......................... 2012 1 0019717

(51) Int. Cl.
*C07D 213/46* (2006.01)
*C07D 401/04* (2006.01)
*C07D 213/61* (2006.01)

(52) U.S. Cl.
CPC ............ *C07D 401/04* (2013.01); *C07D 213/46* (2013.01); *C07D 213/61* (2013.01)

(58) Field of Classification Search
CPC ....................................................... C07D 213/46
USPC .................................................... 546/258, 259
See application file for complete search history.

(56) References Cited

U.S. PATENT DOCUMENTS 6,040,450 A    3/2000  Davies

FOREIGN PATENT DOCUMENTS

| WO | WO 2004/072037 A1 | 8/2004 |
| WO | 2012/066570 | * 5/2012 |
| WO | WO 2012/066570 A2 | 5/2012 |

* cited by examiner

*Primary Examiner* — Patricia L Morris
(74) *Attorney, Agent, or Firm* — Ladas & Parry LLP

(57) ABSTRACT

The present invention relates to a process for the synthesis of the anti-inflammatory agent 5-chloro-3-(4-methanesulfonylphenyl)-6'-methyl-[2,3']bipyridine, referred to as compound of formula (1) or etoricoxib, which is a pharmaceutically active ingredient inhibiting cyclooxygenase-2. In particular, the application concerns a novel process of making the compound of formula (1) by oxidizing a compound of formula (4).

(4)

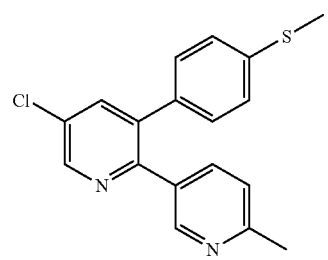

19 Claims, No Drawings

PROCESS FOR THE SYNTHESIS OF ETORICOXIB

The present invention relates to a process for the synthesis of the anti-inflammatory drug 5-chloro-3-(4-methanesulfonylphenyl)-6'-methyl-[2,3']bipyridine, referred to as compound of formula (1), which is an inhibitor of cyclooxygenase-2. In particular, the present invention concerns a process for making the compound of formula (1) and specific intermediates which are useful in the synthesis of the compound of formula (1).

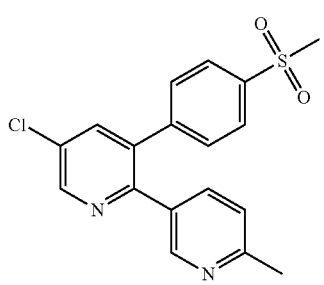

The compound of formula (1), also known under the name etoricoxib, is a potent selective inhibitor of cyclooxygenase-2 with anti-inflammatory, antipyretic and analgesic properties. Etoricoxib has been approved by regulatory administrations for the clinical use as a non-steroidal anti-inflammatory drug. The drug is marketed as a film-coated tablet under the tradename Arcoxia®.

The compound of formula (1) was first disclosed in EP 0 912 518 B1 (also in JP 1999514008, U.S. Pat. No. 5,861,419 and WO 98/03484). EP 0 912 518 B1 discloses the synthesis of the compound of formula (1) by palladium catalyzed coupling of aryl/pyridyl halides with aryl/pyridyl boronic acids or stannanes. The preparation of the compound of formula (1) as disclosed in EP 0 912 518 B1 is difficult for large scale manufacturing and expensive in material cost.

EP 0 975 596 B1 describes a process for making the compound of formula (1), wherein the pyridine moiety is formed by the condensation of 2-chloromalonaldehyde (5) with methylsulfonylbenzylpyridylketone (2) in modest yield.

EP 1 023 266 B1 discloses a process for making the compound of formula (1) by the condensation of 2,3-disubstituted acroleins (6 and 7) with methylsulfonylbenzylpyridylketone (2) in modest yield. EP 1 023 266 B1 also describes a process for making the intermediate compound methylsulfonylbenzylpyridylketone (2) by reacting methylthiobenzylmagnesiumhalide with the Weinreb amide of the pyridine moiety to form methylthiobenzylpyridylketone (3), followed by oxidation of the thio ether (3) to afford methylsulfonylbenzylpyridylketone (2).

EP 1 071 745 B1 (see also U.S. Pat. No. 6,040,319; WO 99/55830) describes a process for making the compound of formula (1) by subjecting methylsulfonylbenzylpyridylketone (2) to a condensation reaction with 2-chloro-1,3-bis(dimethylamino)-trimethinium hexafluorophosphate (8) under basic reaction conditions. Similar methods were also reported (Org. Lett. (2000), 2(15), 2339-2341) for synthesis of both 5-chloro-3-(4-methylthiophenyl)-6'-methyl-[2,3']bipyridine (4) and 5-chloro-3-(4-methanesulfonylphenyl)-6'-methyl-[2,3']bipyridine (1), wherein 2-chloro-1,3-bis(dimethylamino)trimethinium hexafluorophosphate (8) is reacted with methylthiobenzylpyridylketone (3) or methylsulfonylbenzylpyridylketone (2) under basic reaction conditions.

A $^{11}C$ radiolabeled compound of formula (1) is reported (Bioorg. Med. Chem. Lett. 15 (2005) 4268-4271). The preparation of the radiolabeled compound of formula (1) was achieved in a very complex way and in poor yield by oxidizing the penultimate 5-chloro-3-(4-[$^{11}C$]methylthiophenyl)-6'-methyl-[2,3']bipyridine, which was synthesized from the intermediate 5-chloro-3-(4-methylthiophenyl)-6'-methyl-[2,3']bipyridine (4). The methyl group of 5-chloro-3-(4-methylthiophenyl)-6'-methyl-[2,3']bipyridine (4) was replaced with a $^{11}C$-labeled methyl group to give the penultimate 5-chloro-3-(4-[$^{11}C$]methylthiophenyl)-6'-methyl-[2,3']bipyridine. The preparation of 5-chloro-3-(4-methylthiophenyl)-6'-methyl-[2,3']bipyridine (4) was achieved by the condensation of methylthiobenzylpyridylketone (3) with 2-chloro-1,3-bis(dimethylamino)trimethinium hexafluorophosphate (8) using basic reaction conditions.

The synthesis of intermediate 5-chloro-3-(4-methylthiophenyl)-6'-methyl-[2,3']bipyridine (4) is also reported in Bioorg. Med. Chem. Lett. 16 (2006), 3209-3212, ES 2214130A1 and WO 2004/072037 A1. The synthesis involves the palladium catalyzed coupling of a pyridyl stannane with a methylthiophenyl-pyridylchloride. The sulfoxide derivative of the compound of formula (1) is then made by oxidizing 5-chloro-3-(4-methylthiophenyl)-6'-methyl-[2,3'] bipyridine (4) with t-BuOOH.

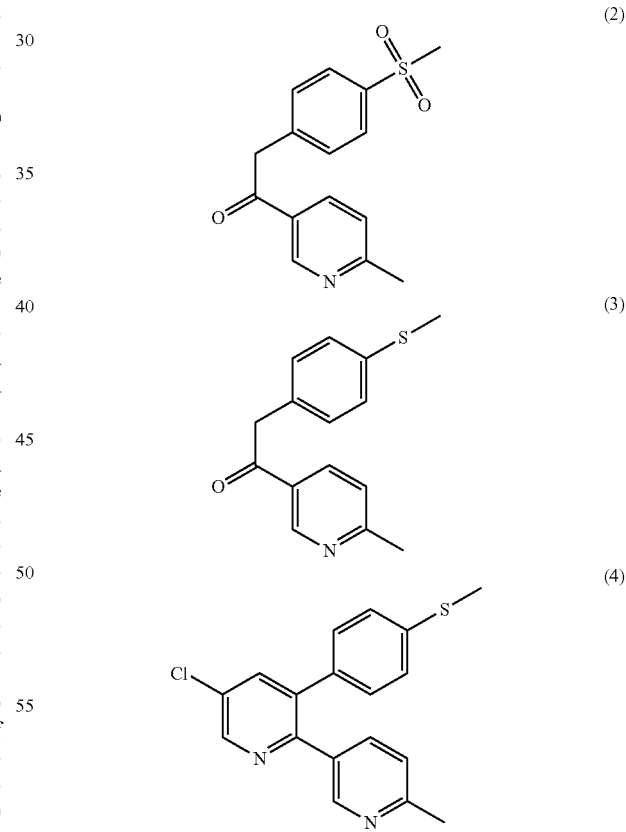

The synthesis of 2-chloromalonaldehyde (5) was reported by Diekmann back in 1904 (Ber. Deut. Chem. Ges. (1904) 37, 4638). The synthesis and use of 2-chloromalonaldehyde (5) were reviewed extensively in 1975 by Rechardt and Halbritter (Angew. Chem. Int. Ed (1975) 14, 86). As readily available and economically inexpensive, 2-chloromalonaldehyde (5) is suitable in the synthesis of the compound of formula (1).

The preparation of the acrolein derivatives (6 and 7) as described in EP 1 023 266 B1 requires additional synthetic steps subsequent to the preparation of 2-chloromalonaldehyde (5) which increases the production costs and environmental risk.

The preparation of 2-chloro-1,3-bis(dimethylamino)trimethinium hexaflurophosphate (8) as reported in EP 1 071 745 B1 involves the use of dangerous chemicals such as phosphorus oxychloride, which can also cause chemical harm to occupational health such as N,N-dimethylformamide. Processes involving these hazardous chemicals increase the risk in process control and cause potential risk to operators and environment.

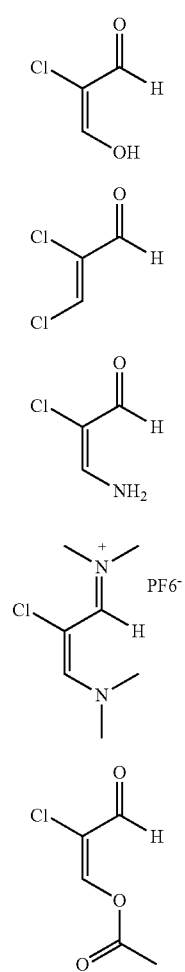

The prior art manufacturing methods for the compound of formula (1) are summarized hereinafter in brief. The compound of formula (1) was first made by palladium catalyzed coupling of aryl/pyridyl halides with corresponding boron or stannane counterparts, which procedure is very complicated and expensive. The compound of formula (1) can be made by condensation of the sulphonyl compound of formula (2) with compounds of formula (5, 6 and 7) using acidic reaction conditions, but in modest yields. The compound of formula (1) can also be made by the condensation of the sulphonyl compound of formula (2) with a compound of formula (8) under basic reaction condition in good yield, but this reaction involves more hazardous chemicals and reaction steps. The thio compound of formula (4) can be made by condensation of the thio compound of formula (3) with the compound of formula (8) under basic reaction condition in good yield. The $^{11}C$ radiolabeled thio compound (4) has been oxidized in a very complex way to its $^{11}C$ radiolabeled sulphonyl (1) counterpart with Oxone® in very poor yield.

It was an object of the present invention to provide a process for the preparation of etoricoxib or a pharmaceutical acceptable salt thereof, wherein the drug is obtained with better yields compared to the manufacturing methods reported in the above prior art documents and wherein the use of large amounts of harmful organic solvents, such as dichloromethane or chloroform, is avoided. This object is solved by the subject matter as defined in the claims.

The present invention relates to a process for the preparation of etoricoxib having the formula (1)

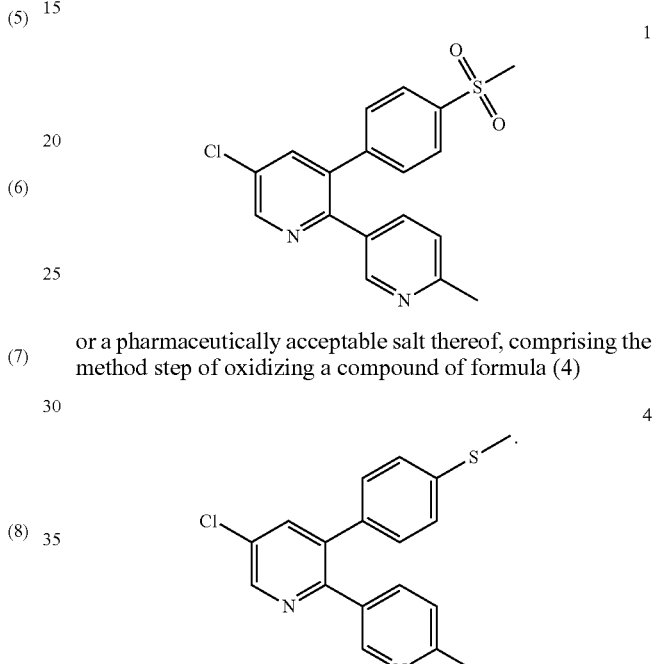

or a pharmaceutically acceptable salt thereof, comprising the method step of oxidizing a compound of formula (4)

According to a preferred embodiment of the present invention, the compound of formula (4) is prepared by condensing a compound of formula (3)

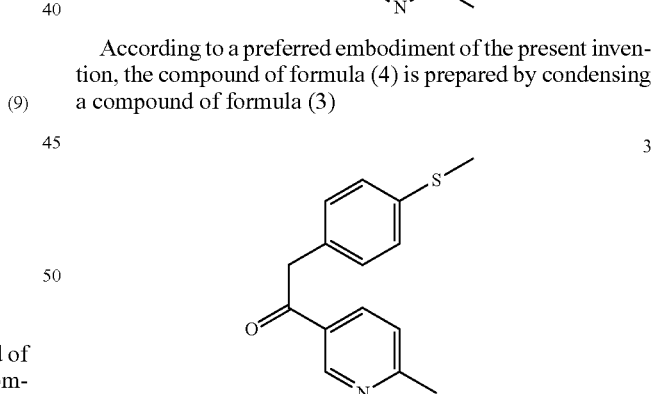

with a compound of formula (10)

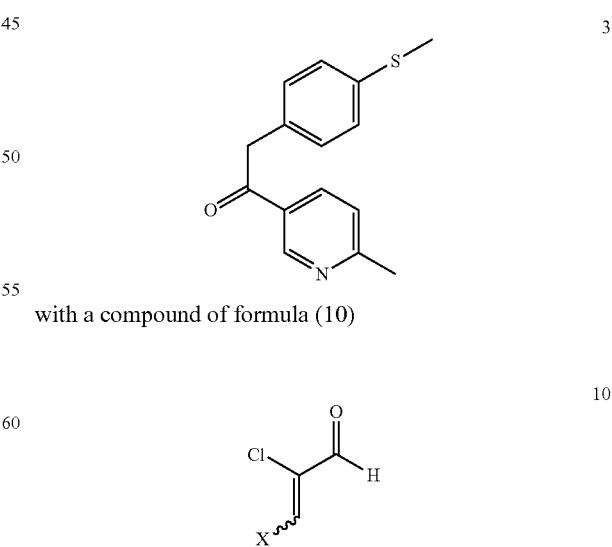

in the presence of an acid, and optionally in the presence of an ammonium reagent, wherein X is $NH_2$, or a group selected from OH, halogen and OR, wherein R is alkylcarbonyl, arylcarbonyl, alkylsulfonyl, arylsulfonyl or silyl.

The term "halogen" refers to fluoro, chloro, bromo and iodo, wherein chloro is preferred.

The term "alkylcarbonyl" refers to a $C_{1-11}$-alkylcarbonyl, preferably a $C_{1-5}$-alkylcarbonyl, and more preferred to a $C_{1-3}$-alkylcarbonyl group.

The term "arylcarbonyl" refers to a $C_{6-10}$-arylcarbonyl, preferably phenylcarbonyl group.

The term "alkylsulfonyl" refers to a $C_{1-12}$-alkylsulfonyl, preferably a $C_{1-6}$-alkylsulfonyl, and more preferred to a $C_{1-4}$-alkylsulfonyl group.

The term "arylsulfonyl" refers to a $C_{6-10}$-arylsulfonyl group, e.g. a phenylsulfonyl or p-toluenesulfonyl group.

The term "silyl" refers to a trialkylsilyl group, preferably a tri($C_{1-4}$-alkyl)silyl group, e.g. a trimethylsilyl (TMS) or tert-butyldimethylsilyl (TBDMS) group.

According to a preferred embodiment of the present invention the compound of formula (10) is 2-chloromalonaldehyde (5) or 2-chloro-3-acetoxyacrolein (9).

The ammonium reagent may be selected from inorganic ammonium salts, e.g. ammonium chloride, ammonium sulfate or ammonium phosphate, and organic ammonium salts, e.g. ammonium acetate, ammonium oxalate or ammonium propionate, while the acid is preferably selected from inorganic acids, e.g. hydrochloric acid, nitric acid, phosphoric acid or sulfuric acid, sulfonic acids, e.g. methanesulfonic acid or p-toluenesulfonic acid, and carboxylic acids, e.g. acetic acid, propionic acid, butyric acid or iso-butyric acid.

According to a preferred embodiment of the present invention the compound of formula (4) is separated from the reaction mixture by basifying the reaction mixture with a basifying agent and extracting the compound of formula (4) from the basified reaction mixture with an organic solvent. Preferably the basifying agent is selected from alkali metal salts and earth alkaline metal salts, e.g. sodium carbonate, sodium bicarbonate, potassium carbonate, potassium bicarbonate, sodium hydroxide, potassium hydroxide, sodium phosphate, potassium phosphate, calcium carbonate or calcium bicarbonate, while the organic solvent may be selected from ester and ether solvents, each optionally in admixture with a hydrocarbon solvent, e.g. butyl acetate, iso-butyl acetate, tert-butyl acetate, propyl acetate, iso-propyl acetate, ethyl acetate, methyl acetate, butyl formate, iso-butyl formate, tert-butyl formate, propyl formate, iso-propyl formate, ethyl formate, methyl formate, diethyl ether and tert-butyl methyl ether, each optionally in admixture with hexane, cyclohexane, heptane, octane or petroleum ether.

Further purification of the compound of formula (4) can be made by recrystallization with a solvent selected from butyl acetate, iso-butyl acetate, tert-butyl acetate, propyl acetate, iso-propyl acetate, ethyl acetate, methyl acetate, butyl formate, iso-butyl formate, tert-butyl formate, propyl formate, iso-propyl formate, ethyl formate, methyl formate, diethyl ether, tert-butyl methyl ether, hexane, cyclohexane, heptane, octane, petroleum ether, and mixtures thereof; preferably with a solvent selected from hexane, cyclohexane, heptane, octane, petroleum ether, and mixtures thereof, which are optionally heated.

In another embodiment of the present invention the compound of formula (4) is converted into a salt by dissolving the compound of formula (4) in an organic solvent and precipitating the salt of the compound of formula (4) by adding an acid, preferably an acid selected from inorganic acids, e.g. hydrochloric acid, nitric acid, phosphoric acid or sulfuric acid, and sulfonic acids, e.g. methanesulfonic acid or p-toluenesulfonic acid. In this embodiment the organic solvent is preferably selected from ethyl acetate, methyl acetate, tert-butyl methyl ether, dioxane, THF, and mixtures thereof.

In a preferred embodiment of the present invention the oxidation of the compound of formula (4) comprises the method steps of:
i) combining the compound of formula (4) or a salt thereof, an organic solvent and optionally an acid,
ii) optionally adding an oxidation catalyst,
iii) adding an oxidizing agent, and
iv) isolating the compound of formula (1).

Preferably, the organic solvent is an alcohol, e.g. methanol, ethanol, propanol or 2-propanol. The acid, if present, may be selected from sulfuric acid, hydrochloric acid and acetic acid. It is preferable to add an oxidation catalyst, such as sodium, potassium or ammonium molybdate or tungstate, to the reaction mixture. Preferably, the oxidizing agent is hydrogen peroxide or peracetic acid.

The method step (iv) may be conducted by:
a) adding a reducing agent to the reaction mixture,
b) removing the organic solvent,
c) adding water,
d) optionally washing the aqueous solution obtained in step (c) by extraction with an organic solvent,
e) precipitating the compound of formula (1) by basifying the aqueous solution obtained in step (c) or (d) with a basifying agent, and
f) optionally subjecting the product obtained in step (e) to recrystallization.

The reducing agent is preferably selected from $NaHSO_3$, $KHSO_3$, $Na_2SO_3$, $K_2SO_3$, $Na_2S_2O_4$, $K_2S_2O_4$, $Na_2S_2O_3$, $K_2S_2O_3$, NaHS, KHS, $Na_2S$, $K_2S$, S, $FeCl_2$, $FeSO_4$, Fe, Zn, $KBH_4$ and $NaBH_4$, while the basifying agent may be selected from alkali metal salts and earth alkaline metal salts, e.g. sodium carbonate, sodium bicarbonate, potassium carbonate, potassium bicarbonate, sodium hydroxide, potassium hydroxide, sodium phosphate, potassium phosphate, calcium carbonate or calcium bicarbonate.

The recrystallization in step (f) is usually conducted with an aqueous alcoholic solution, e.g. an aqueous methanol, ethanol, propanol, iso-propanol, butanol, iso-butanol or tert-butanol solution.

The present invention relates to a convenient, economical and non-hazardous process, in which the compound of formula (1) is made by ring annulation between methylthiobenzylpyridylketone (3) and, preferably, the readily available 2-chloromalonaldehyde (5) or 2-chloro-3-acetoxyacrolein (9) in high yield, and subsequent oxidation of the thio ether group of the formed 5-chloro-3-(4-methylthiophenyl)-6'-methyl-[2,3']bipyridine (4) to the sulfonyl group of the compound of formula (1).

In the prior art preparations of the compound of formula (1), it was shown that the critical pyridine ring annulations is achieved under basic reaction conditions, i.e. by condensation of 2-chloro-1,3-bis(dimethylamino)trimethinium hexafluorophosphate (8) with both methylthiobenzylpyridylketone (3) and methylsulfonylbenzylpyridylketone (2), in better yields than under acidic reaction conditions, i.e. by condensation of methylthiobenzylpyridylketone (3) with 2-chloromalonaldehyde (5) or 2,3-disubstituted acroleins (6 and 7). However, the preparation of 2-chloro-1,3-bis(dimethylamino)trimethinium hexafluorophosphate (8) required dangerous and very hazardous chemical phosphorus oxychloride which is very difficult to handling in manufacturing operations and for environmental protection. In prior art, the use of the starting material 2-chloromalonaldehyde (5) in the preparation of the compound of formula (1) was attempted only with the condensation of methylsulfonylbenzylpyridylketone (2) under acidic reaction conditions and provided relatively poor yields. A successful preparation of the compound of formula (1) is reported herein, wherein the condensation of the easily available compounds of formula (10), preferably 2-chloromalonaldehyde (5) or 2-chloro-3-acetoxyacrolein (9), with methylthiobenzylpyridylketone (3) under acidic reaction conditions is achieved. The reaction yields of the critical pyridine ring annulations were comparable to the process under basic reaction conditions using 2-chloro-1,3-bis(dimethylamino)trimethinium hexafluorophosphate (8). Another benefit from the condensation of preferably 2-chloromalonaldehyde (5) or 2-chloro-3-acetoxyacrolein (9) with methylthiobenzylpyridylketone (3) is that the thio compound of formula (4) has much better solubility in organic solvents, such as ethyl acetate, methyl acetate, tert-butyl methyl ether, hexane, cyclohexane, heptane, octane and petroleum ether, than the compound of formula (1), which was obtained in the condensation reactions using the methylsulfonylbenzylpyridylketone (2). The existence of the polar sulphonyl group in the compound of formula (1) may explain the decrease of the solubility in organic solvents such as ethyl acetate and methyl acetate, while the penultimate thio compound of formula (4) possesses the less polar thio group. The good solubility of the thio compound of formula (4) in less harmful organic solvents, such as ethyl acetate, methyl acetate, tert-butyl methyl ether, hexane, cyclohexane, heptane, octane and petroleum ether, allows the use of reasonable amounts of such solvents in the isolation process. In the preparation of the sulphonyl compound of formula (1) from methylsulfonylbenzylpyridylketone (2) as described in the state of the art, a large amount of solvents such as ethyl acetate or other toxic solvents such as dichloromethane or chloroform must be used in the isolation process after the condensation reaction took place due to the poor solubility of the resulting sulphonyl compound of formula (1) in organic solvents such as ethyl acetate, methyl acetate and tert-butyl methyl ether compared to the thio compound of formula (4).

The oxidation of the thio group to the sulphonyl group has been studied extensively for a quiet long period of time. The oxidation of the thio group to the sulphonyl group with hydrogen peroxide usually offers high yields. However, the oxidation has to be carefully controlled to avoid oxidation of the pyridine rings existing in the structures of the starting thio compound of formula (4) or the compound of formula (1).

In the prior art, only a complex oxidation of a $^{11}$C radiolabeled thio compound to the $^{11}$C radiolabeled compound of formula (1) was reported in very poor yield. According to the present invention, an easy oxidation method of the thio compound of formula (4) to the compound of formula (1) in almost quantitative yield is presented.

Many simple and practicable procedures are available for the preparation of 2-chloromalonaldehyde (5) including preparation from 1,1,2,3,3-pentachloropropane (Houben-Weyl-Muller, Methoden der Organischen Chemie, 4$^{th}$ Ed. Vol 7/1, Thieme Verlag, 1954, page 119), preparation from mucochloric acid (Ber. Deut. Chem. Ges. 1904, 37, 4638) and preparation from chloroacetylchloride (Collect. Czech. Chem. Commun. 1961, 26, 3051). As readily available and economically inexpensive, 2-chloromalonaldehyde (5) is suitable in the synthesis of the compound of formula (1).

The present invention discloses a process for preparing 5-chloro-3-(4-methylthiophenyl)-6'-methyl-[2,3']bipyridine (4) by condensation of methylthiobenzylpyridylketone (3), preferably with 2-chloromalonaldehyde (5) or its acetyl ester derivative, the 2-chloro-3-acetoxyacrolein (9). A general procedure of the condensation is described hereinafter: methylthiobenzylpyridylketone (3) and 2-chloromalonaldehyde (5) or 2-chloro-3-acetoxyacrolein (9) were added to a solution of acid and ammonium salts, the mixture were heated and stirred over a period of time to complete the ring annulation. The amount of acid was reduced by distillation under reduced pressure. The remaining residue was basified with an alkaline solution. The solution was extracted with an extraction solvent several times. The combined organic solutions were treated with charcoal, filtered and dried with sodium sulfate. The solution was then filtered and evaporated under reduced pressure. The 5-chloro-3-(4-methylthiophenyl)-6'-methyl-[2,3']bipyridine (4) was obtained as an off-white solid. Further purification of the compound of formula (4) was made by recrystallization with organic solvents involving dissolution of the solid in an organic solvent under heating, charcoal treatment of the solution, removal of charcoal by filtration, evaporation part of the solvent, cooling of the remaining solution, filtration and washing of the precipitate, and drying of the solid.

The process for preparing 5-chloro-3-(4-methylthiophenyl)-6'-methyl-[2,3']bipyridine (4) by condensation of methylthiobenzylpyridylketone (3) with 2-chloromalonaldehyde (5) or 2-chloro-3-acetoxy-acrolein (9) is described in more detail below:

a) The condensation took place in acidic reaction conditions: the acid used is one of the following acids, such as acetic acid, propionic acid, butyric acid, iso-butyric acid, or any combination of two or more of the above acids. The acid or combination of acids is used in relatively excessive quantity.

b) The condensation took place at elevated reaction temperature, wherein the reaction temperature starts from room temperature (20° C.) to elevated temperature (140° C.).

c) The condensation took place with an ammonium reagent including ammonia or various ammonium salts with the ability liberating ammonium ion for the pyridine ring annulations: including but not limited to inorganic ammonium salts such as ammonium chloride, ammonium sulfate and ammonium phosphate; including but not limited to organic ammonium salts such as ammonium acetate, ammonium oxalate and ammonium propionate.

d) The condensation took place with the reactants methylthiobenzylpyridylketone (3) and 2-chloromalonaldehyde (5) or 2-chloro-3-acetoxyacrolein (9).

e) The condensation took place with various molar ratios of reactants such as ammonia or ammonium salt, methylthiobenzylpyridylketone (3) and 2-chloromalonaldehyde or 2-chloro-3-acetoxyacrolein (9), the molar ratios can vary against each other in a range of 1 to 10.

f) The condensation took place over a period of from 1 to 24 hours until completion of ring annulation, preferably 15 to 20 hours.

g) The alkaline used was one of the following: sodium carbonate, sodium bicarbonate, potassium carbonate, potassium bicarbonate, sodium hydroxide, potassium hydroxide, sodium phosphate and potassium phosphate.

h) The extraction solvent was one of the following or any mixture of them: butyl acetate, iso-butyl acetate, tert-butyl acetate, propyl acetate, iso-propyl acetate, ethyl acetate, methyl acetate, butyl formate, iso-butyl formate, tert-butyl formate, propyl formate, iso-propyl formate, ethyl formate, methyl formate, ethyl ether and tert-butyl methyl ether, the extraction solvent can also be combined with following solvents: hexane, cyclohexane, heptane, octane and petroleum ether.

i) Solvent for recrystallization was one of the following or any mixture of them: butyl acetate, iso-butyl acetate, tert-butyl acetate, propyl acetate, iso-propyl acetate, ethyl acetate, methyl acetate, butyl formate, iso-butyl formate, tert-butyl formate, propyl formate, iso-propyl formate, ethyl formate, methyl formate, diethyl ether, tert-butyl methyl ether, hexane, cyclohexane, heptane, octane and petroleum ether.

The preparation of the salts of 5-chloro-3-(4-methylthiophenyl)-6'-methyl-[2,3']bipyridine (4) is described below:
a) The salts of 5-chloro-3-(4-methylthiophenyl)-6'-methyl-[2,3']bipyridine (4) were composed by one of the acids: hydrochloric acid, sulfuric acid, nitric acid, phosphoric acid, toluenesulfonic acid and methanesulfonic acid.
b) The solvent was one of the following or any mixture of them: ethyl acetate, methyl acetate, tert-butyl methyl ether, dioxane and THF.
c) The acids used to form such salts were one of the following: hydrochloric acid, sulfuric acid, nitric acid, phosphoric acid, toluenesulfonic acid and methanesulfonic acid.

General procedure of the salt preparation: 5-chloro-3-(4-methylthiophenyl)-6'-methyl-[2,3']bipyridine (4) was dissolved in a solvent, and to the solution was added the acid. The precipitate formed was filtered, washed with the solvent and dried to give an off-white solid.

The present invention discloses a process to prepare the final compound of formula (1) by oxidation of 5-chloro-3-(4-methylthiophenyl)-6'-methyl-[2,3']bipyridine (4).
a) The oxidation took place with alcohol of one of the following: methanol, ethanol, propanol and 2-propanol.
b) The oxidation took place with an acid of one of the following: sulfuric acid, hydrochloric acid and acetic acid.
c) The oxidation took place with the catalyst: sodium molybdate, sodium tungstate, ammonium molybdate, ammonium tungstate, potassium molybdate and potassium tungstate.
d) The oxidation took place with oxidation agent: hydrogen peroxide or peracetic acid.
e) The oxidation took place at room temperature to elevated temperature of 60° C.
f) The oxidation took place over a period of from 5 minutes to 2 hours.
g) The reagent used to stop oxidation was $NaHSO_3$, $KHSO_3$, $Na_2SO_3$, $K_2SO_3$, $Na_2S_2O_4$, $K_2S_2O_4$, $Na_2S_2O_3$, $K_2S_2O_3$, NaHS, KHS, $Na_2S$, $K_2S$, S, $FeCl_2$, $FeSO_4$, Fe, Zn, $KBH_4$ and $NaBH_4$.
h) The alkaline used was one of the following or any mixture of them: sodium carbonate, sodium bicarbonate, potassium carbonate, potassium bicarbonate, sodium hydroxide, potassium hydroxide, sodium phosphate and potassium phosphate.
i) The aqueous alcohol solution used for recrystallization was aqueous methanol solution, aqueous ethanol solution, aqueous propanol solution, aqueous iso-propanol solution and aqueous butanol, aqueous iso-butanol and aqueous tert-butanol solution in various concentrations.

General procedure of the oxidation: The 5-chloro-3-(4-methylthiophenyl)-6'-methyl-[2,3']bipyridine (4) or one of its salts was dissolved in a solution of alcohol and acid with catalyst. To the solution was added slowly a solution of oxidation agent under room temperature or elevated temperature up to 60° C. The reaction mixture was kept stirring for a period to the completion of the oxidation and a reductive agent was added. The organic solvent was removed under reduced pressure and to remain residue was added water. The aqueous solution was washed with ethyl acetate several times, treated with charcoal and filtered. The solution was basified by alkaline solution and the precipitate was collected, washed with water. The solid was recrystallized with aqueous alcohol solution and dried in vacuum to give an off-white solid of compound of formula (1).

The preparation process of compound of formula (1) disclosed in the present invention is a convenient, economical and non-hazardous process, in which many hazardous and dangerous chemicals used in the prior art processes are avoided.

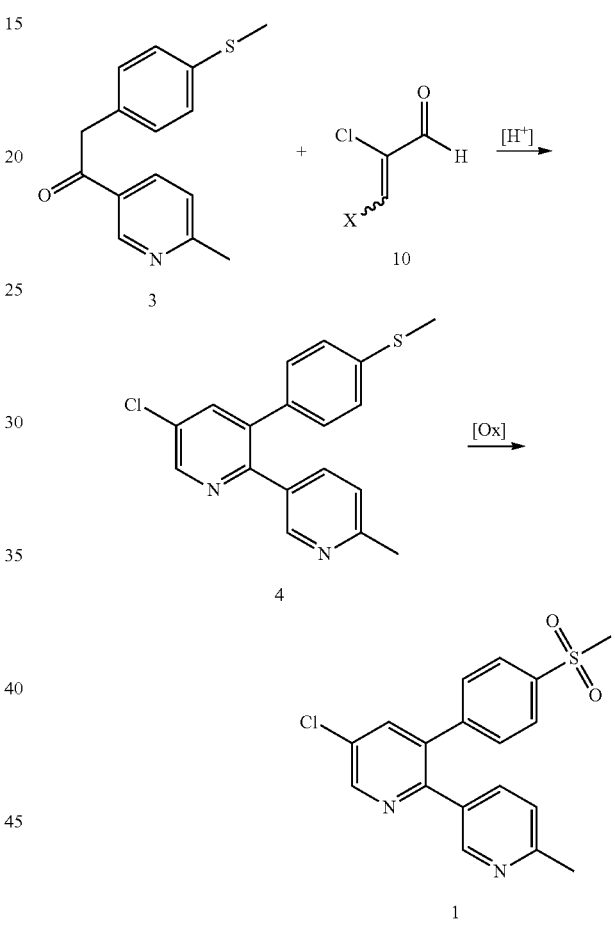

The present invention is illustrated further by the following examples in which, unless stated otherwise: all process procedures were carried out at ambient or room temperature, that is within the range of about 15-25° C.; solvent evaporations were carried out under reduced pressure at 600-4000 Pascals (4.5-30 mm Hg) with bath temperatures of up to about 60° C.; the course of reactions was tracked by thin layer chromatography (TLC) or High Pressure Liquid Chromatography (HPLC); the structure and purity of all products were assured by at least one of the following techniques: TLC, HPLC, mass spectrometry, nuclear magnetic resonance (NMR) spectrometry or microanalytical data; NMR spectrometry was determined at 300 MHz or 400 MHz using the indicated solvent; polymorphism may result in isolation of materials with different melting points in some preparation; chemical symbols have their usual meaning; the following abbreviations, v (volume), w (weight), b.p. (boiling point), m.p. (melting point), L (litter(s)), ml (milliliter(s)), g (gram(s)), mg (milligram(s)), mol (mole(s)), mmol (millimole(s)) and eq (equivalent(s)) have also been used.

PREPARATIVE EXAMPLE 1

5-Chloro-3-(4-methylthiophenyl)-6'-methyl-[2,3'] bipyridine (4) by Condensation of methylthiobenzylpyridylketone (3) with 2-chloromalonaldehyde (5) in Acidic Condition Methylthiobenzylpyridylketone (3) (20 g, 0.078 mol) and 2-chloromalonaldehyde (5) (24.5 g, 0.23 mol) were added to a solution of propionic acid (140 mL) and ammonium acetate (53.9 g, 0.7 mol). The mixture was heated to 130° C., and stirred for 16 hours. The amount of acid was reduced by distillation under reduced pressure. The remaining mixture was basified with 100 mL $NaCO_3$ solution (20%). The solution was extracted with ethyl acetate (70 mL) 3 times. The combined organic solutions were treated with charcoal, filtered and dried with sodium sulfate. The solution was then filtered and evaporated under reduced pressure. The 5-chloro-3-(4-methylthiophenyl)-6'-methyl-[2,3']bipyridine (4) was obtained. Further purification of the solid was made by recrystallization involving dissolution of the solid in cyclohexane under heating above 40° C. up to refluxing, charcoal treatment of the solution, removal of the charcoal by filtration, evaporation part of the solvent under reduced pressure, cooling of the remaining solution to 0-15° C., filtration and washing of precipitate with small amounts of cyclohexane, drying in vacuum to give an off-white solid of the compound of formula (4) (17.3 g, 68%), m.p. 108.0-109.5° C.; $^1H$ NMR (400 MHz, $CDCl_3$), δ (ppm): 8.62 (d, J=2.8 Hz, 1H), 8.45 (d, J=2.0 Hz, 1H), 7.69 (d, J=2.8 Hz, 1H), 7.56 (dd, J=2.4, 8.0 Hz, 1H), 7.16 (m, 2H), 7.07 (m, 3H), 2.53 (s, 3H), 2.47 (s, 3H). $^{13}C$ NMR (400 MHz, $CDCl_3$), δ (ppm): 157.9, 152.3, 149.9, 147.3, 139.2, 137.9, 137.3, 136.8, 134.4, 131.9, 130.9, 129.7, 126.3, 122.5, 24.2, 15.3; MS: 327 (M+1).

PREPARATIVE EXAMPLE 2

5-Chloro-3-(4-methylthiophenyl)-6'-methyl-[2,3'] bipyridine (4) by Condensation of methylthiobenzylpyridylketone (3) with 2-chloromalonaldehyde (5) in Acidic Condition Methylthiobenzylpyridylketone (3) (20 g, 0.078 mol) and 2-chloromalonaldehyde (5) (24.5 g, 0.23 mol) were added to a solution of acetic acid (150 mL) and ammonium acetate (53.9 g, 0.7 mol). The mixture was heated to reflux, and stirred for 16 hours. The amount of acid was reduced by distillation under reduced pressure. The remaining mixture was basified with 100 mL NaOH solution (10%). The solution was extracted with ethyl acetate (70 mL) 3 times. The combined organic solutions were treated with charcoal, filtered and dried with sodium sulfate. The solution was then filtered and evaporated under reduced pressure. The 5-chloro-3-(4-methylthiophenyl)-6'-methyl-[2,3']bipyridine (4) was obtained as an off-white solid (13.0 g, 51%), m.p. 108.0-109.5° C.

PREPARATIVE EXAMPLE 3

5-Chloro-3-(4-methylthiophenyl)-6'-methyl-[2,3'] bipyridine (4) by Condensation of methylthiobenzylpyridylketone (3) with 2-chloro-3-acetoxyacrolein (9)

Methylthiobenzylpyridylketone (3) (20 g, 0.078 mol) and 2-chloro-3-acetoxyacrolein (9) (34.5 g, 0.23 mol) were added to a solution of propionic acid (150 mL) and ammonium acetate (53.9 g, 0.7 mol). The mixture was heated to 130° C., and stirred for 16 hours. The amount of acid was reduced by distillation under reduced pressure. The remaining mixture was basified with 100 mL NaOH solution (10%). The solution was extracted with ethyl acetate (70 mL) 3 times. The combined organic solutions were treated with charcoal, filtered and dried with sodium sulfate. The solution was then filtered and evaporated under reduced pressure. The 5-chloro-3-(4-methylthiophenyl)-6'-methyl-[2,3']bipyridine (4) was obtained as an off-white solid (11.5 g, 45%), m.p. 108.1-109.7° C.

PREPARATIVE EXAMPLE 4

5-Chloro-3-(4-methylthiophenyl)-6'-methyl-[2,3'] bipyridine (4) by Condensation of methylthiobenzylpyridylketone (3) with 2-chloro-3-acetoxyacrolein (9)

Methylthiobenzylpyridylketone (3) (20 g, 0.078 mol) and 2-chloro-3-acetoxyacrolein (9) (34.5 g, 0.23 mol) were added to a solution of acetic acid (150 mL) and ammonium acetate (53.9 g, 0.7 mol). The mixture was heated to 130° C., and stirred for 16 hours. The amount of acid was reduced by distillation under reduced pressure. The remaining mixture was basified with 100 mL NaOH solution (10%). The solution was extracted with ethyl acetate (70 mL) 3 times. The combined organic solutions were treated with charcoal, filtered and dried with sodium sulfate. The solution was then filtered and evaporated under reduced pressure. The 5-chloro-3-(4-methylthiophenyl)-6'-methyl-[2,3']bipyridine (4) was obtained as an off-white solid (10.4 g, 41%).

PREPARATIVE EXAMPLE 5

Hydrochloride Salts of 5-Chloro-3-(4-methylthiophenyl)-6'-methyl-[2,3']bipyridine (4)

5-Chloro-3-(4-methylthiophenyl)-6'-methyl-[2,3']bipyridine (4) (50 g, 0.15 mol) was dissolved in a tert-butyl methyl ether (200 mL), and to the solution was passed a steam of gaseous hydrogen chloride. The precipitate formed was filtered, washed with the ether and dried to give an yellow solid of hydrochloride salts of 5-chloro-3-(4-methylthiophenyl)-6'-methyl-[2,3']bipyridine (4) (50.57 g, 91%), m.p.>250° C.

PREPARATIVE EXAMPLE 6

Compound of Formula (1) by Oxidation of 5-Chloro-3-(4-methylthiophenyl)-6'-methyl-[2,3'] bipyridine (4)

To a solution of 5-chloro-3-(4-methylthiophenyl)-6'-methyl-[2,3']bipyridine (4) (50 g, 0.15 mol) and sulfuric acid (6 g, 0.061 mol) in methanol (300 mL) was added sodium molybdate (1.2 g, 0.004 mol). The solution was heated to 55° C., and was added hydrogen peroxide (40 mL, 30%). The reaction mixture was kept stirring for 15 min and $NaHSO_3$ (60 mL, 30%) was added. The reaction mixture then was cooled to room temperature, organic solvent was removed under reduced pressure and water (100 mL) was added. The aqueous solution was washed with ethyl acetate (50 mL) 2 times, treated with charcoal and filtered. The solution was basified by NaOH solution (20%) and the precipitate was collected, washed with water (50 mL). The solid was recrystallized with aqueous ethanol solution and dried in vacuum to give an off-white solid (51.6 g, 94%) of compound of formula (1), m.p. 135.5-135.9° C.; $^1$H NMR (400 MHz, CDCl$_3$), δ (ppm): 8.72 (d, J=2.0 Hz, 1H), 8.38 (d, J=2.0 Hz), 7.91 (dd, J=1.6, 6.4 Hz, 2H), 7.74 (d, J=2.4 Hz, 1H), 7.56 (dd, J=2.4, 8.0 Hz, 1H), 7.41 (dd, J=2.0, 6.8 Hz, 2H), 7.09 (d, J=8.4 Hz, 1H), 3.09 (s, 3H), 2.54 (s, 3H). $^{13}$C NMR (400 MHz, CDCl$_3$), δ (ppm): 158.6, 152.4, 149.8, 148.4, 143.8, 140.3, 137.9, 137.4, 135.3, 131.3, 131.2, 130.4, 127.9, 122.8, 44.5, 24.2; MS: 359 (M+1).

The invention claimed is:

1. A process for the preparation of etoricoxib having the formula (1)

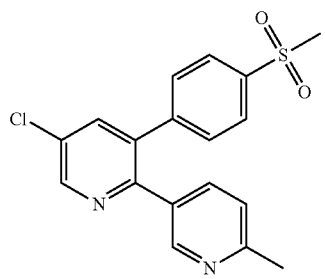

or a pharmaceutically acceptable salt thereof,
comprising the method step of oxidizing a compound of formula (4)

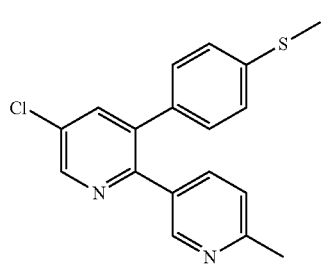

wherein the compound of formula (4) is prepared by condensing a compound of formula (3)

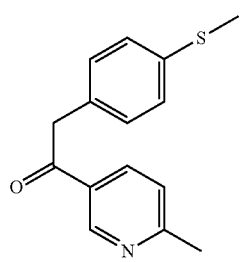

with a compound of formula (10)

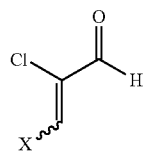

in the presence of an acid, and optionally in the presence of an ammonium reagent, wherein X is NH$_2$ or a group selected from OH, halogen and OR, wherein R is alkylcarbonyl, arylcarbonyl, alkylsulfonyl, arylsulfonyl or silyl.

2. The process according to claim 1, wherein the compound of formula (10) is 2-chloromalonaldehyde (5) or 2-chloro-3-acetoxyacrolein (9).

3. The process according to claim 1, wherein the ammonium reagent is an inorganic or organic ammonium salt.

4. The process according to claim 1, wherein the acid is selected from inorganic acids, sulfonic acids, and carboxylic acids.

5. The process according to claim 1, wherein the compound of formula (4) is separated from the reaction mixture by basifying the reaction mixture with a basifying agent and extracting the compound of formula (4) from the basified reaction mixture with an organic solvent, and optionally purified by recrystallization with a recrystallization organic solvent.

6. The process according to claim 5, wherein the basifying agent is selected from alkali metal salts and earth alkaline metal salts.

7. The process according to claim 5 wherein the organic solvent is selected from ester and ether solvents, each optionally in admixture with a hydrocarbon solvent, further optionally in admixture with hexane, cyclohexane, heptane, octane or petroleum ether.

8. The process according to claim 5, wherein the recrystallization organic solvent is selected from butyl acetate, iso-butyl acetate, tert-butyl acetate, propyl acetate, iso-propyl acetate, ethyl acetate, methyl acetate, butyl formate, iso-butyl formate, tert-butyl formate, propyl formate, iso-propyl formate, ethyl formate, methyl formate, diethyl ether, tert-butyl methyl ether, hexane, cyclohexane, heptane, octane, petroleum ether, and mixtures thereof.

9. The process according to claim 1, wherein the compound of formula (4) is converted into a salt by dissolving the compound of formula (4) in an organic solvent and precipitating the salt of the compound of formula (4) by adding an acid.

10. The process according to claim 9, wherein the organic solvent is selected from ethyl acetate, methyl acetate, tert-butyl methyl ether, dioxane, THF, and mixtures thereof.

11. The process according to claim 1, wherein the oxidation of the compound of formula (4) comprises the method steps of:
    i) combining the compound of formula (4) or a salt thereof, an organic solvent and optionally an acid,
    ii) optionally adding an oxidation catalyst,
    iii) adding an oxidizing agent, and
    iv) isolating the compound of formula (1).

12. The process according to claim 11, wherein the organic solvent is an alcohol.

13. The process according to claim 11, wherein the acid is selected from sulfuric acid, hydrochloric acid and acetic acid.

14. The process according to claim 11, wherein the oxidation catalyst is selected from sodium molybdate, sodium tungstate, ammonium molybdate, ammonium tungstate, potassium molybdate and potassium tungstate.

15. The process according to claim 11, wherein the oxidizing agent is hydrogen peroxide or peracetic acid.

16. The process according to claim 11, wherein method step (iv) comprises the method steps of:
    a) adding a reducing agent to the reaction mixture,
    b) removing the organic solvent,
    c) adding water,
    d) optionally washing the aqueous solution obtained in step (c) by extraction with an organic solvent, e) precipitating the compound of formula (1) by basifying the aqueous solution obtained in step (c) or (d) with basifying agent, and f) optionally subjecting the product obtained in step (e) to recrystallization.

17. The process according to claim 16, wherein the reducing agent is selected from $NaHSO_3$, $KHSO_3$, $Na_2SO_3$, $K_2SO_3$, $Na_2S_2O_4$, $K_2S_2O_4$, $Na_2S_2O_3$, $K_2S_2O_3$, NaHS, KHS, $Na_2S$, $K_2S$, S, FeCb, $FeSO_4$, Fe, Zn, $KBH_4$ and $NaBH_4$.

18. The process according to claim 16 wherein the basifying agent is selected from alkali metal salts and earth alkaline metal salts.

19. The process according to claim 16, wherein the recrystallization in step (f) is conducted with an aqueous alcoholic solution.

* * * * *